United States Patent [19]

Shrimpton

[11] Patent Number: 4,605,558

[45] Date of Patent: Aug. 12, 1986

[54] PROCESS FOR CELL SEPARATION

[76] Inventor: Wallace Shrimpton, 1015 Grandview Dr., South San Francisco, Calif. 94080

[21] Appl. No.: 602,461

[22] Filed: Apr. 20, 1984

[51] Int. Cl.$^4$ .................. A01N 1/02; A61K 35/52; A61K 35/14
[52] U.S. Cl. ........................ 424/105; 435/2; 424/101
[58] Field of Search ............... 435/2; 424/105, 101

[56] References Cited

U.S. PATENT DOCUMENTS 3,894,529  7/1975  Shrimpton ............... 435/2
4,327,177  4/1982  Shrimpton ............... 435/2

Primary Examiner—Sam Rosen

[57] ABSTRACT

A process for the separation of X sperm and Y sperm by phenotypic differences in a gravity separation process wherein an osmolality gradient is provided within the separation vessel, the osmolality preferably being in inverse relationship to the density gradient.

4 Claims, No Drawings

PROCESS FOR CELL SEPARATION

SUMMARY OF THE INVENTION

The present invention is an improvement over my prior U.S. Pat. Nos. 3,894,529 and 4,327,177, the subject matter of which is herein incorporated by reference.

In my prior patents, it was recognized that it was important to maintain the proper osmotic pressure during a separation process to avoid any possible harmful compression or expansion of the sperm. However, it was assumed that the osmotic pressure would not vary throughout the separation column. For instance, in U.S. Pat. No. 3,894,529 column 12, line 54, it is stated that the osmolality would be substantially constant throughout the density gradient. Substantially the same statement is made in U.S. Pat. No. 4,327,177, column 11, line 40. Thus, it was not recognized that the hydrostatic pressure within the column had to be taken into account or that one could compensate for the change in hydrostatic pressure by a change in the osmolality.

One of the reasons for the success of the present modification of the density gradient process has been the ability to precisely control the volume of the cells by controlling the osmotic pressure of the media.

By increasing or decreasing the osmotic pressure of the solution surrounding the cells, one is able to change cell volume by adjusting the amount of free water in the cell.

It is well-known that, like red blood cells, spermatozoa can be caused to swell by placing them in a solution of lower osmotic pressure, i.e. more water molecules per volume than within the cell and caused to shrink by being placed in solutions of higher osmotic pressure.

Osmotic pressure also causes changes in density of the cells as $P=M/V$ where P=Density M=Mass of cells V=Volume of cells.

Cells with different sized nuclei appear to be effected differently by osmotic pressure, i.e. the ratio of swelling of the cell with a smaller nucleus is different from those with a larger nucleus because of the difference in the amount of free water within the cell and possibly differences in the membrane tension.

Osmolality control, therefore, is an important factor in the improved development of the density gradient separation process.

One of the devices developed as a means of effecting density gradient separation is an iso-osmotic gradient. Density gradients used heretofore are usually made by the increase in the number of some molecules in the solution. The osmolarity of the solution increases with the increase of the molecules added to the solution. Thus, previously density and osmolarity could not be varied independently.

In accordance with the present invention, one can adjust the osmolarity of the solution and then adjust the density of the solution by adding globules (1-2 microns) of lipids, e.g. cream, oils or any substance which can be stably emulsified in the solution. These globules are above the molecular size range so they do not affect the osmotic pressure of the solution.

In working with the density gradient, it has been found necessary to:
(a) adjust the osmotic range in which the sperm are separated, and
(b) make osmotic adjustments within the column to compensate for the differences in hydrostatic pressure on the sperm which varies with the depth of immersion of the spermatozoa in the solution.

DESCRIPTION OF THE PREFERRED EMBODIMENTS

In carrying out the present invention, means must be provided for independently varying the osmolality and the density within a column. Normally when dealing with relatively large differences in density, the effect of osmolality would be overshadowed. In the present invention, one is dealing with very slight density gradients and under these conditions the influence of osmolality on separation is important.

In general, the process of the present invention is carried out by first providing a material having a low density and adjusting the osmolality to a given value, ordinarily by adding water. Now one takes a material of higher density and adjusts the osmolality, again, for example, by adding water, to obtain a material having a low osmolality and a higher density than the low density material prepared as above. Ordinarily in a practical embodiment of the invention, one would also use a medium density material and adjust the osmolality of this to some value between the high and the low mentioned above by mixing the materials prepared above. Now one can use these materials to provide a separation column having a high density at the bottom and a low density at the top but preferably with an osmolality in inverse relationship. This, in effect, compensates for the increase in hydrostatic pressure at the bottom of the column so that the separation can take place on a gradient basis more efficiently.

The following is a specific method of preparing various milk media for use in a separation process.

A. Pasteurization

1. In a double boiler, heat 2 quarts of half and half to 92° C., stir every 5-10 minutes.
2. Remove from heat and allow to cool to 10° C.
3. Remove any butterfat which rises to the surface of the half and half.
4. Filter half and half through glass wool.
5. Measure volume of half and half in a sterile 1000 ml graduated cylinder. Return half and half to sterile plastic bottle.
6. Repeat steps 1-5 for 1 quart of homogenized (hereafter: homo) milk.
7. Repeat steps 1-5 for one-half pint of whipping cream.
8. Pasteurize 2 quarts of skim milk in the following manner:
   a. Bring temperature to 92° C.
   b. Cool to 90° C.
   c. Raise to 92° C.
   d. Repeat steps a, b and c for a total of 10 minutes.
9. Repeat steps 2-6 with non-fat milk.

B. Addition of Antibiotics

1. After pasteurization and filtering, add the following antibiotics to each type of media:
   3 cc per liter of Penicillin
   3 cc per liter of Streptomycin
   15 cc per liter of Polymixim B Sulfate
2. Put aside 100 ml of homo for glyceration.
3. After addition of antibiotics, add 0.2 grams per 100 ml of fructose to each type of media.
4. Cap container securely and refrigerate.

C. Osomolarity

1. Measure the osmolarity of each type of milk used.
2. Adjust the osmolarity of each type of milk by the addition of sterile distilled water to the following values: non-fat 278.5, homo 279.5, half and half 280.5. Calculations for osmolarity corrections are as follows:

To obtain the volume of distilled water necessary for adjustment, divide initial osmolarity by desired osmolarity, subtract 1.00, multiply the results by the volume of milk in question.

Sample calculation:
   Initial osmolarity: 305 m/os
   Volume: 1500 ml
   Desired osmolarity: 278 m/os $305/278 = 1.097$ $1.097 - 1.000/0.097 =$ $0.097 \times 1500 = 146$ ml to add 3. Always add less than the calculated amount of distilled water because it is difficult to correct the osmolarity if it is overshot.

D. Density

1. Measure the densities of each type of milk. Density should be measured after adjusting the osmolarity.
2. When a medium of a specific density is required, calculate the percentages necessary of the component media.

Sample calculation: Rinser Medium
   Required density: 1.0280
   Components: half and half and homo
   Half and half density: 1.0240
   Homo density: 1.0330 a. Begin by taking 50% of each density and adding the products.

d Half and half $= 1.0240 \times 0.5 = 0.5120$ d Homo $= 1.0330 \times 0.5 = 0.5165/1.0285$ 1.0285 is the density obtained by mixing 50% half and half and 50% homo.

b. If this result is heavier than desired, increase the percentage of the milk of lighter density.
   c. If this result is lighter than desired, increase the percentage of the milk of heavier density.

3. After calculations, measure the desired proportions in a graduated cylinder and mix together.
4. Mix well and check density at 21° C.
5. If density is not correct, adjust by trial and error addition of the appropriate medium.
6. Pour medium into sterile plastic bottles. Use new sterile bottle caps for each run. Label each bottle as follows:
   a. Type of medium contained (Rinser, Low, etc)
   b. Density
   c. Osmolarity
   d. Date
7. Repeat steps 1-6 for all types of media to be made.
8. The following table provides the range of percentages for the components of the various media. These are based on combinations after the addition of fructose, antibiotics and adjustments in osmolarity and density.

Rinser: 1.0280
   50-70% half and half
   30-50% homo
   Low: 1.0240-1.0245
   70-90% half and half
   10-30% homo
   Extender: 1.0275
   92% half and half
   8% egg yolk
   High: 1.0340-1.0345
   75-90% skim milk
   25-10% whipping cream
   Must be homogenized after density and osmolarity are set.
   X-Low: 1.0220
   80-90% half and half
   10-20% whipping cream
   Buffer:
   100% non-fat milk
   Extra High
   100% skim milk The rinser is just used to rinse out the tubes prior to making a separation. The extender is used as a diluent. The other solutions are employed to prepare density gradient columns as is taught in my prior patents, referenced above.

Utilizing solutions made up in accordance with the above procedure having desired densities and osmolarities, the following tests were made:

OSMOLARITY

A. The effects of changing osmolality from the optimum for a given bull

Semen was collected on three different days —1/24/83, 1/31/83 and 2/8/83 from Holstein bull #1204 at Carnation Genetics. The semen was diluted in an extender made from a mixture of the high and low density media prepared as above. Table I below gives the differences in the media used which were identical in every other respect.

TABLE I

| | Osmolarity Control | |
|---|---|---|
| | Control | Experimental |
| Trial 1 | | |
| Low Density | 280 M/Osmols | 278 M/Osmols |
| High Density | 278 M/Osmols | 276 M/Osmols |
| Trial 2 | | |
| Low Density | 280 M/Osmols | 282 M/Osmols |
| High Density | 278 M/Osmols | 280 M/Osmols |
| Trial 3 | | |
| Low Density | 280.0 M/Osmols | 278 M/Osmols |
| High Density | 278.1 M/Osmols | 280 M/Osmols |

Samples were withdrawn from each lot of semen to act as controls.

Separation of the semen was attempted using the density gradient procedure as set forth in my prior patents referenced above.

Following the full separation procedure the semen, both the control and separation, from each run was glycerated and frozen in liquid nitrogen.

Semen from each run was then thawed and cell volumes were measured and compared. Experience in the past has indicated that spermatozoa, when measured under a specific set of conditions, behaved as follows:

Those which produced female calves were repeatedly significantly of larger volume than those which did not. For example, two samples from unseparated controls do not show differences in size. Samples from female separated sperm have been shown by field trials to be always greater in volume than those which are not separated.

TABLE II

Results of Osmolality Experiment

| Trial | Date | Bull No. | Run No. | Difference of Average Osmo Between Ex.*[1] & Control*[2] | Degree of Separation Control | Exp. |
|---|---|---|---|---|---|---|
| 1 | 1/24/83 | 1204 | 202 | −2 M/OS | +2.280 | 2.860 |
| 2 | 1/31/83 | 1204 | 204 | +2 M/OS | +0.970 | −1.870 |
| 3 | 2/8/83 | 1204 | 206 | Reverse Gradient*[3] | +2.770 | 0.660 |
|   |   |   |   | $\overline{X} =$ | 2.006 | 0.356 |

*[1]Refers to Experiment
*[2]Osmo usually used: low density 280 m/os  high density 278 m/os
*[3]Low density 278 m/os  High density 280 m/os Above results show that with Bull 1204[(1)] if osmolality is above range, or if the usual inverse osmotic gradient is reversed, less separation takes place.

(2) Reduction of range increased separation slightly.

Therefore, the optimum range for this bull appears to be low density of medium from 278 to 280 m/osmols, and high density of medium from 276 to 278 m/osmols.

B. The effect of using the same osmotic range for each bull

Semen was collected on six different days from Bull 219 and run at a variety of osmotic pressures with all other conditions being kept equal. Table III below gives a summary of the results.

TABLE III

Summary of Results Using Different Osmolalities on the Same Bull

| Trial | Date | Run No. | Bull No. | Osmo Used | Degree of Separation Control | Exp. |
|---|---|---|---|---|---|---|
| 1 | 2/15/83 | 207 | 219 | Usual as for #1204 | −3.88 |   |
| 2 | 2/22/83 | 208 | 219 | Usual as for #1204 | 0.25 |   |
| 3 | 3/15/83 | 213 | 219 | Usual as for #1204 −4 m/os | 1.55 | 4.55 |
| 4 | 3/23/83 | 215 | 219 | Usual as for #1204 | 0.04 | 3.55 |

TABLE III-continued

Summary of Results Using Different Osmolalities on the Same Bull

| Trial | Date | Run No. | Bull No. | Osmo Used | Degree of Separation Control | Exp. |
|---|---|---|---|---|---|---|
|   |   |   |   | −2 m/os |   |   |

Evidence to date above tends to show that Bull 219 requires a lower osmolality setting in the column than Bull 1204. Thus, the osmolality in the column seems to be a discrete factor for each bull. At this time, it is not known whether this varies with changes of season.

The above observation appears valid in the light of the fact that it would be highly improbable for spermatozoa of all bulls to have the same osmotic requirements.

Although this invention was developed primarily for the separation of bovine sperm, it can be applied to any cellular biological material which can be separated or fractionated by gravity separation.

I claim:

1. In the known process for the separation of X sperm and Y sperm by phenotypic differences in a density separation process wherein sperm are suspended in a nutrient medium having a gradient in density from top to bottom within a vessel, the improvement comprising independently maintaining an osmolality gradient in the nutrient medium within said vessel.

2. The process of claim 1 wherein the osmolality gradient is inverse to that of said density gradient.

3. The process for the preparation of a medium for the gravity separation of cellular biological material enclosed within a semi-permeable membrane, comprising:
   a. providing at least one low density first nutrient medium and adjusting the osmolality to a desired value
   b. providing at least one high density second nutrient medium and adjusting the osmolality to a lower value than the osmolality of said first nutrient medium,
   c. placing said first and second nutrient media in a vessel to provide a gravity separation means having a high density and a low osmolality at one side and a low density and a high osmolality at the other side.

4. A medium for the gravity separation of X and Y spermatozoa wherein said medium has a high density at the bottom and a low density at the top and a low osmolality at the bottom and a high osmolality at the top.

* * * * *